(12) United States Patent
Hope et al.

(10) Patent No.: US 6,395,948 B1
(45) Date of Patent: May 28, 2002

(54) HIGH VISCOSITY POLYALPHAOLEFINS PREPARED WITH IONIC LIQUID CATALYST

(75) Inventors: Kenneth D. Hope, Kingwood, TX (US); Michael S. Driver, San Francisco; Thomas V. Harris, Benicia, both of CA (US)

(73) Assignee: Chevron Chemical Company LLC, Houston, TX (US)

( * ) Notice: Subject to any disclaimer, the term of this patent is extended or adjusted under 35 U.S.C. 154(b) by 0 days.

(21) Appl. No.: 09/588,103

(22) Filed: May 31, 2000

(51) Int. Cl.[7] .............................. C07C 2/04; C07C 2/24; C07C 2/02
(52) U.S. Cl. .................. 585/510; 585/512; 585/513; 585/514; 585/520
(58) Field of Search .................................. 585/510, 512, 585/513, 514, 520

(56) References Cited

U.S. PATENT DOCUMENTS

| 4,827,064 A | 5/1989 | Wu .............................. 585/10 |
| 5,304,615 A | 4/1994 | Ambler et al. .............. 526/189 |

FOREIGN PATENT DOCUMENTS

| EP | 0 791 643 A1 | 8/1997 |
| WO | WO 95/21872 | 8/1995 |

*Primary Examiner*—Walter D. Griffin
*Assistant Examiner*—Tam M. Nguyen
(74) *Attorney, Agent, or Firm*—Charles W. Stewart

(57) ABSTRACT

A process for preparing very high viscosity polyalphaolefins using an acidic ionic liquid oligomerization catalyst in the absence of an organic diluent and the products formed thereby.

36 Claims, No Drawings

HIGH VISCOSITY POLYALPHAOLEFINS PREPARED WITH IONIC LIQUID CATALYST

FIELD OF THE INVENTION

The present invention relates to the preparation of high viscosity polyalphaolefins prepared using an ionic liquid catalyst.

BACKGROUND OF THE INVENTION

Alphaolefins may be oligomerized to prepare synthetic lubricating oil base stocks which have desirable lubricating properties such as a low pour point and a high viscosity index (VI). However, very high viscosity polyalphaolefins, such as disclosed in U.S. Pat. No. 4,827,064, are expensive to manufacture using conventional oligomerization processes. U.S. Pat. No. 5,304,615 teaches the oligomerization of butene using an ionic liquid catalyst. European Patent Application 97300875.8 describes a process for oligomerizing alphaolefins, such as decene, using an ionic liquid catalyst to produce polyalphaolefins having a viscosity up to about 20 centistokes (cSt) at 100° C. Unfortunately, the process taught in this application has not been shown to be suitable for making very high viscosity material, i.e., polyalphaolefins having a viscosity above 22 cSt at 100° C.

Additionally, the prior art teaches the use of imidazolium, pyridinium, or phosphorium as one component in the ionic liquid in addition to aluminum halide or gallium halide. Ternary compositions with ammonium halides are described in WO 95/121872 as being useful for olefinic oligomerization.

Applicants have found that it is possible to readily make polyalphaolefins having very high viscosity using an ionic liquid catalyst by carrying out the oligomerization reaction in the absence of organic solvents which have hitherto been used as a diluent for the feed. Accordingly, Applicants have been able to make polyalphaolefins from feeds comprised primarily of olefins, such as decene and dodecene, having viscosities in excess of 22 cSt and even in excess of 30 cSt. Polyalphaolefins made using the process of the present invention also have been shown to display excellent viscosity index (VI) values, low pour points, and low Noack volatility values. As used in this disclosure, the words "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the combination. The phrase "consisting of" is intended as a transition meaning the exclusion of all but the recited elements with the exception of only minor traces of impurities.

SUMMARY OF THE INVENTION

The present invention is directed to a process for producing a very high viscosity polyalphaolefin product comprising contacting a feed consisting essentially of at least one alphaolefin having from 4 to about 14 carbon atom with an effective oligomerizing amount of an acidic ionic liquid oligomerization catalyst, maintaining said feed and oligomerization catalyst Under preselected oligomerization conditions for a sufficient time to oligomerize the alphaolefin to the polyalphaolefin product, and recovering the high viscosity polyalphaolefin product. As noted above, it has been found that very high viscosity products may be obtained using the process of the present invention by carrying out the oligomerization reaction in the absence of organic diluent. Using the process of the invention, polyalphaolefins having viscosities in excess of 22 cSt and even in excess of 30cSt may be readily prepared. Especially preferred in preparing the polyalphaolefin product are feeds comprising decene or dodecene.

The acidic ionic liquid oligomerization catalyst usually will be comprised of at least two components, and in most instances it will be a binary catalyst, i.e., it will consist of only two components. The first component is a compound selected from the group consisting of aluminum halide, alkyl aluminum halide, gallium halide, and alkyl gallium halide. Preferred compounds for use as the first component of the oligomerization catalyst are an aluminum halide or an alkyl aluminum halide, such as, for example, aluminum trichloride. The second component is quaternary ammonium, quaternary phosporium, or tertiary sulfonium, such as, for example, a liquid salt selected from one or more of hydrocarbyl substituted ammonium halides, hydocarbyl substituted imidazolium halide, hydrocarbyl substituted pyridinium halide, alkylene substituted pyridinium dihalide, or hydrocarbyl substituted phosphonium halide. Particularly preferred as the second component are alkyl substituted ammonium halides, such as trimethylamine hydrochloride or alkyl substituted imidizolium halides, such as 1-ethyl-3-methyl-imidazolium chloride. The mole ratio of the two components will usually fall within the range of from about 1:1 to about 5:1 of said first component to said second component, and more preferably the mole ratio will be in the range of from about 1:1 to about 2:1.

The use of a binary catalyst composition consisting essentially of trimethylamine hydrochloride and aluminum trichloride is particularly advantageous for carrying out the process of the present invention due to the ease of preparation, the ready commercial availability of the components, and the relatively low cost.

The amount of catalyst present to promote the oligomerization of the alphaolefin should be not less than an effective oligomerizing amount, that is to say, the minimum amount of the catalyst necessary to olgomerize the alphaolefin to the desired product. This may vary to some degree depending on the composition of the catalyst, the ratio of the two components of the catalyst to one another, the feed, the oligomerzation conditions chosen, and the like. However, a determination of the effective catalytic amount should be well within the ability of one skilled in the art with no more than routine testing necessary to establish the amount needed to carry out the invention. The present invention is also directed to the unique polyalphaolefin product prepared using the present invention. This product is characterized by a viscosity of not less than 22 cSt at 1 00° C., and more preferably will have a viscosity of at least 30 cSt at 100° C. In addition, the polyalphaolefin product will display a low pour point, preferably less than −300° C., and low volatility, preferably with a Noack number of 3 or less. Preferably, the product will have a dimer content of less than 2 weight percent.

DETAILED DESCRIPTION OF THE INVENTION

As noted above, it is essential that the oligomerization reaction be conducted in the absence of any organic diluent. In carrying out the process of the present invention, the alphaolefin feed may be added to the catalytic mixture or the catalyst may be added to the alphaolefin feed. In either case, the feed and the product formed during the oligomerization will form a separate phase from the ionic liquid which allows the two phases to be readily separated. In order to facilitate mixing of the catalyst and the feed, it is desirable to either stir the oligomerization mixture or bubble the alphaolefin feed through the ionic liquid catalyst. Following completion of the oligomerization reaction, the mixing should be halted, and the product and residual feed should be allowed to form a distinct layer apart from the catalyst phase. In previous processes, the feed and product phase usually also contained an organic diluent, such as hexane. Applicants have discovered the presence of the organic diluent of the previous processes interferes with the oligomerization reaction and prevents the formation of the desired very high viscosity polyalphaolefin product.

The feed will consist essentially of one or more alphaolefins having from 4 to about 14 carbon atoms in the molecule, generally from about 8 to about 12 carbon atoms. Especially preferred are feeds containing 1-decene and 1-dodecene. While the feed may consist of a mixture of different alphaolefins, it is essential that the feed not contain any organic diluent. As explained above and as further illustrated in the examples below, it has been found that the presence of an organic diluent interferes with the oligomerization reaction and prevents the formation of the desired very high viscosity polyalphaolefin product. This differs from the prior processes which included an organic diluent, such as hexane or heptane, as part of the organic phase of the reaction mixture.

The acidic ionic liquid oligomerization catalyst is comprised of two components which form a complex. The first component of the catalyst which will usually comprise a compound selected from the group consisting of aluminum halide, alkyl aluminum halide, gallium halide, and alkyl gallium halide. Especially preferred for the first component are aluminum halide or alkyl aluminum halide. Aluminum trichoride has been used successfully as the first component for preparing the oligomerization catalyst used in practicing the present invention.

The second component making up the catalyst is an ionic liquid which is primarily salt or mixture of salts which melts below room temperature. Ionic liquids may be characterized by the general formula $Q^+$ $A^-$, wherein $Q^+$ is quaternary ammonium, quaternary phosphonium, or quaternary sulfonium, and $A^-$ is a negatively charged ion such as $Cl^-$, $Br^-$, $OCl_4^-$, $NO_3^-$, $BF_4^-$, $BCl_4^-$, $PF_6^-$, $SbF_6^-$, $AlCl_4^-$, $ArF_6^-$, $TaF_6^-$, $CuCl_2^-$, $FeCl_3^-$, $SO_3CF_3^-$, $SO_3C_7^-$, 3-sulfurtrioxyphenyl. Preferred for use as the second component are those quaternary ammonium halides containing one or more alkyl moieties having from 1 to about 9 carbon atoms, such as, for example, trimethylamine hydrochloride, or hydrocarbyl substituted imidazolium halides, such as, for example, 1-ethyl-3-methyl-imidazolium chloride.

The presence of the first component should give the ionic liquid a Lewis (or Franklin) acidic character. Generally, the greater the mole ratio of the first component to the second component, the greater the acidity of the ionic liquid mixture. When aluminum trichloride and trimethylamine hydrochoride are used as the first and second components, respectively, of the acidic ionic liquid oligomerization catalyst, they preferably will be present in a mole ratio of from about 1:1 to about 2:1.

The oligomerization reaction takes place over a wide temperature range, but preferably is carried out at about ambient temperature or slightly below. The oligomerization reaction is somewhat exothermic and it may be desirable to control the reaction temperature with an aqueous quench. Preferably, the temperature of the reaction mixture will be maintained below about 50° C. and most preferably Will be maintained below about 30° C.

Following completion of the oligomerization reaction, the organic layer containing the alphaolefin product and residual olefin feed is separated from the ionic liquid phase. The unreacted olefin and dimers may be removed from the product by conventional means, such as by distillation, and recycled back for further conversion. Likewise, the acidic ionic liquid catalyst that remains after recovery of the organic phase may be recycled to the oligomerization zone.

Following recovery of the polyalphaolefin product, it is generally desirable to hydrogenate the unsaturated double bonds which remain in the product mixture. This is readily accomplished by conventional means well known to those skilled in the art. The hydrogenation of the unsaturated bonds is usually carried out with hydrogen in the presence of a hydrogenation catalyst such as, for example, catalyst containing nickel, palladium, platinum, cobalt or the like.

The present invention may be further illustrated by the following example which is not intended to be a limitation on the process.

EXAMPLE 1

A catalyst mixture was prepared using a 2 to 1 ratio of aluminum trichloride to trimethylamine hydrochloride. The catalyst (39.2 g) was placed in a 1 liter round bottom flask to which 401.2 g of 1-decene was added dropwise. The initial temperature of the oligomerization mixture was 0° C. which was allowed to raise to 22° C. An inert atmosphere was maintained by a nitrogen sweep gas/bubbler. The reaction was allowed to proceed for 1 hour and was quenched with aqueous potassium hydroxide. The product was water washed and hydrogenated using a nickel catalyst. The residual monomer and dimer were removed by distillation. The distilled oligomer was found to display the following properties:

| | |
|---|---|
| 100° C. Kinematic Viscosity | 31.6 cSt |
| 40° C. Kinematic Viscosity | 283 cSt |
| Viscosity Index | 152 |
| Pour Point | −39° C. |
| Noack Volatility | 1.68% |

EXAMPLE 2

The general procedure was the same as in Example 1, above, except for the addition of 1 85 grams of heptane diluent which was mixed with 400 grams of decene. Catalyst was prepared in a 2 to 1 molar ratio of aluminum trichloride to trimethylamine hydrochloride and 40.1 grams were added to the reaction in a dropwise manner. The initial reaction temperature was −60° C. The product was water washed and hydrogenated using a nickel catalyst. The residual monomer and dimer were removed by distillation to less than 1%. The distilled oligomer was found to display the following properties:

| | |
|---|---|
| 100° C. Kinematic Viscosity | 15.0 cSt |
| 40° C. Kinematic Viscosity | 109 cSt |

| | |
|---|---|
| Viscosity Index | 143 |
| Pour Point | −45° C. |

It should be noted that the kinematic viscosity of the oligomer of Example 2 was significantly less at both 100° C. and 40° C. than that for the oligomer of Example 1. The viscosity index of the product of Example 2 was also lower.

What is claimed is:

1. A process for producing a very high viscosity polyalphaolefin product comprising contacting a feed consisting essentially of at least one alphaolefin of either 1-decene or 1-dodecene with an effective oligomerizing amount of an acidic ionic liquid oligomerization catalyst, maintaining said feed and oligomerization catalyst under preselected oligomerization conditions for a sufficient time to oligomerize the alphaolefin to the polyalphaolefin product, and recovering the high viscosity polyalphaolefin product.

2. The process of claim 1 wherein said at least one alpha olefin of said feed is 1-decene.

3. The process of claim 1 wherein said at least one alpha olefin feed is 1-dodecene.

4. The process of claim 1 wherein the acidic ionic oligomerization catalyst comprises a first component and a second component, said first component comprising a compound selected from the group consisting of aluminum halide, alkyl aluminum halide, gallium halide, and alkyl gallium halide, and said second component is an ionic liquid comprising a liquid salt containing quaternary ammonium, quaternary phosporium, or quaternary sulfonium.

5. The process of claim 4 wherein said first component is aluminum halide or alkyl aluminum halide.

6. The process of claim 5 wherein said first component is aluminum trichloride.

7. The process of claim 4 wherein said second component is selected from one or more of hydrocarbyl substituted ammonium halide, hydrocarbyl substituted imidazolium halide, hydrocarbyl substituted pyridinium halide, alkylene substituted pyridinium dihalide, or hydrocarbyl substituted phosphonium halide.

8. The process of claim 7 wherein the second component is an alkyl substituted ammonium halide containing one or more alkyl moieties having from 1 to about 9 carbon atoms.

9. The process of claim 8 wherein the second component comprises at least trimethyl amine hydrochloride.

10. The process of claim 7 wherein the second component is an alkyl substituted imidazolium halide.

11. The process of claim 10 wherein the second component comprises at least 1-ethyl-3-methyl-imidazolium chloride.

12. The process of claim 4 wherein the ratio of first component to the second component of the oligomerization catalyst is within the range of from about 1:1 to about 5:1.

13. The process of claim 5 wherein the ratio of the first component to the second component is within the range of from about 1:1 to about 2:1.

14. The process of claim 1 including the additional step of hydrogenating the unsaturated double bonds present in the polyalphaolefin product.

15. The process of claim 1 wherein the dimer in the product is reduced to less than 2 weight percent.

16. A process for producing a very high viscosity polyalphaolefin product which is characterized by a viscosity of at least 22 centistokes at 100° C., said process comprising contacting a feed consisting essentially of at least one alphaolefin of either 1-decene or 1-dodecene with an effective oligomerizing amount of a acidic binary ionic liquid oligomerization catalyst having a first component consisting of an aluminum halide or an alkyl aluminum halide and a second component consisting of a quaternary ammonium selected from selected from a quaternary ammonium halide containing one or more alkyl moieties having from 1 to about 9 carbon atoms or a hydrocarbyl substituted imidazolium halide; maintaining said feed and oligomerization catalyst under preselected oligomerization conditions for a sufficient time to oligomerize the alphaolefin to the polyalphaolefin product; and recovering the high viscosity polyalphaolefin product.

17. The process of claim 16 wherein the acidic binary ionic liquid oligomerization catalyst comprises a first component of aluminum trichloride and a second component of trimethylamine hydrochloride.

18. The process of claim 16 wherein the acidic binary ionic liquid oligomerization catalyst comprises a first component of aluminum trichloride and a second component of 1-ethyl-3-methyl-imidazolium chloride.

19. The process according to claims 17 or 18 wherein the mole ratio of aluminum trichloride to the second component is within the range of from about 1:1 and 2:1.

20. A process for producing a very high viscosity polyalphaolefin product comprising contacting a feed, said feed comprises either decene or dodecene but has an absence of an organic diluent, with an effective oligomerizing amount of an acidic ionic liquid oligomerization catalyst, maintaining said feed and oligomerization catalyst under preselected oligomerization conditions for a sufficient time to oligomerize said decene or dodecene to the polyalphaolefin product, and recovering the high viscosity polyalphaolefin product.

21. The process of claim 20 wherein the acidic ionic oligomerization catalyst comprises a first component and a second component, said first component comprising a compound selected from the group consisting of aluminum halide, alky aluminum halide, gallium halide, and alkyl gallium halide, and said second component is an ionic liquid comprising a liquid salt containing quaternary ammonium, quaternary phosporium, or quaternary sulfonium.

22. The process of claim 21 wherein said first component is aluminum halide or alkyl aluminum halide.

23. The process of claim 22 wherein said first component is aluminum trichloride.

24. The process of claim 21 wherein said second component is selected from one or more of hydrocarbyl substituted ammonium halide, hydrocarbyl substituted imidazolium halide, hydrocarbyl substituted pyridinium halide, alkylene substituted pyridinium dihalide, or hydrocarbyl substituted phosphonium halide.

25. The process of claim 24 wherein the second component is an alkyl substituted ammonium halide containing one or more alkyl moieties having from 1 to about 9 carbon atoms.

26. The process of claim 25 wherein the second component comprises at least trimethyl amine hydrochloride.

27. The process of claim 24 wherein the second component is an alkyl substituted imidazolium halide.

28. The process of claim 27 wherein the second component comprises at least 1-ethyl-3-methyl-imidazolium chloride.

29. The process of claim 21 wherein the ratio of first component to the second component of the oligomerization catalyst is within the range of from about 1:1 to about 5:1.

30. The process of claim 22 wherein the ratio of the first component to the second component is within the range of from about 1:1 to about.

31. The process of claim 20 including the additional step of hyrgenating the unsaturated double bonds present in the polyalphaolefin product.

32. The process of claim 20 wherein the dimer in the product is reduced to less than 2, weight percent.

33. A process for producing a very high viscosity polyalphaolefin product which is characterized by a viscosity of at least 22 centistokes at 100° C., said process comprising contacting a feed, said feed comprises either decene or dodecene but has an absence of an organic diluent, with an effective oligomerizing amount of an acidic binary ionic liquid oligomerization catalyst having a first component consisting of an aluminum halide or an alkyl aluminum halide and a second component consisting of a quaternary ammonium selected from a quaternary ammonium halide containing one or more alkyl moieties having from 1 to about 9 carbon atoms or a hydrocarbyl substituted imidazolium halide; maintaining said feed and oligomerization catalyst under preselected oligomerization conditions for a sufficient time to oligomerize the decene or dodecene to the polyalphaolefin product; and recovering, the high viscosity polyalphaolefin product.

34. The process of claim 33 wherein the acidic binary ionic liquid oligomerization catalyst comprises a first component of aluminum trichloride and a second component of trimethylamine hydrochloride.

35. The process of claim 33 wherein the acidic binary ionic liquid oligomerization catalyst comprises a first component of aluminum trichloride and a second component of 1-ethyl-3-methyl-imidazolium chloride.

36. The process according to claims 34 or 35 wherein the mole ratio of aluminum trichloride to the second component is within the range of from about 1:1 and 2:1.

* * * * *